United States Patent
Scott et al.

(10) Patent No.: US 10,100,336 B2
(45) Date of Patent: *Oct. 16, 2018

(54) SYNGAS FERMENTATION PROCESS AND MEDIUM

(71) Applicant: INEOS BIO S.A., Lisle, IL (US)

(72) Inventors: Syrona Scott, Fayetteville, AR (US); Ryan Senaratne, Fayetteville, AR (US); Ching-Whan Ko, Fayetteville, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/889,700

(22) Filed: May 8, 2013

(65) Prior Publication Data

US 2013/0316420 A1 Nov. 28, 2013

Related U.S. Application Data

(60) Provisional application No. 61/650,098, filed on May 22, 2012, provisional application No. 61/650,093, filed on May 22, 2012, provisional application No. 61/650,077, filed on May 22, 2012, provisional application No. 61/650,084, filed on May 22, 2012, provisional application No. 61/726,225, filed on Nov. 14, 2012.

(51) Int. Cl.
| | | |
|---|---|---|
| *C12P 7/06* | (2006.01) | |
| *C12N 1/20* | (2006.01) | |
| *C12P 7/08* | (2006.01) | |
| *C12P 7/16* | (2006.01) | |
| *C12P 7/54* | (2006.01) | |
| *C12P 7/56* | (2006.01) | |

(52) U.S. Cl.
CPC ............... *C12P 7/06* (2013.01); *C12N 1/20* (2013.01); *C12P 7/065* (2013.01); *C12P 7/08* (2013.01); *C12P 7/16* (2013.01); *C12P 7/54* (2013.01); *C12P 7/56* (2013.01); *Y02E 50/17* (2013.01)

(58) Field of Classification Search
CPC .... C12P 7/06; C12P 7/065; C12P 7/08; C12P 7/17; C12P 7/54; C12P 7/56; C12N 1/20; Y02E 50/17
See application file for complete search history.

(56) References Cited

U.S. PATENT DOCUMENTS

| | | |
|---|---|---|
| 5,173,429 A | 12/1992 | Gaddy |
| 5,593,886 A | 1/1997 | Gaddy |
| 5,807,722 A | 9/1998 | Gaddy |
| 5,972,661 A | 10/1999 | Kubera |
| 6,136,577 A | 10/2000 | Gaddy |
| 7,285,402 B2 | 10/2007 | Gaddy |
| 2007/0275447 A1 | 11/2007 | Lewis |
| 2010/0227377 A1 | 9/2010 | Adams |
| 2011/0217742 A1* | 9/2011 | Sun ............ C12N 1/20 435/126 |

FOREIGN PATENT DOCUMENTS

| | | |
|---|---|---|
| WO | WO 98/00558 | 1/1998 |
| WO | WO 00/68407 | 11/2000 |
| WO | 0208438 | 1/2002 |
| WO | WO 2007/117157 | 10/2007 |
| WO | WO 2009/022925 | 2/2009 |
| WO | WO 2009/064200 | 5/2009 |
| WO | WO 2009/113878 | 9/2009 |
| WO | WO 2009/114127 | 9/2009 |
| WO | 2012/074544 | 6/2012 |
| WO | 2012/074545 | 6/2012 |

OTHER PUBLICATIONS

Maedeh, Mohammadi et al., "Bioconversion of Synthesis Gas to Second Generation Biofuels:" A Review, Renewable and Sustainable Energy Reviews; 15; Sep. 15, 2011, pp. 4255-4273.
Saxena, Jyotisna et al., "Effect of Trace Metals on Ethanol Production from Synthesis Gas . . . "; J Ind. Microbiol Biotechnol; Apr. 2011; 38 (4); 513-21.
International Searching Authority, International Search Report issued in PCT/US2013/041249, dated Nov. 13, 2013, 11 pages.
International Searching Authority, International Search Report issued in PCT/US2013/041212, dated Nov. 13, 2013, 11 pages.
Jyotisna Saxena et al: "Optimization of a corn steep medium for production of ethanol from synthesis gas fermentation by". World Journal of Microbiology and Biotechnology, Kluwer Academic Publishers, DO, vol. 28, No. 4, Nov. 26, 2011 (Nov. 26, 2011), pp. 1553-1561.
Wikipedia, Ammonium hydroxide, Accessed Apr. 28, 2015, Online at: en.wikipedia.org/wiki/Ammonium_hydroxide.
Coder J L, et al., Influence of Process parameters on growth of Clostridium ljungdahlii and Clostridium 1 autoethanogenum on synthesis gas, Enzyme and Microbial Technology, May 2009, pp. 281-288, vol. 44, No. 5, D Stoneham, MA, US.
International Searching Authority, International Search Report issued in PCT/US2013/041250, dated Mar. 17, 2014, 5 pages.

* cited by examiner

*Primary Examiner* — Jennifer M. H. Tichy
(74) *Attorney, Agent, or Firm* — James P. Krueger

(57) ABSTRACT

A process for fermenting syngas and a fermentation medium provides high ethanol productivity while removing medium components that were previously thought to be essential. The process is effective for providing a specific STY of at least about 1 g ethanol/(L·day·gram cells). In this aspect, the fermentation medium has less than about 1.04 ppm boron, less than about 0.16 ppm manganese, less than about 0.26 ppm molybdenum, or less than about 0.16 ppm copper.

11 Claims, No Drawings

SYNGAS FERMENTATION PROCESS AND MEDIUM

This application claims the benefit of U.S. Provisional Application Nos. 61/650,098, 61/650,093, 61/650,077, 61/650,084 all filed on May 22, 2012 and U.S. Provisional Application No. 61/726,225 filed on Nov. 14, 2012, all of which are incorporated in their entirety herein by reference.

Processes and mediums are provided for fermentation of syngas. More specifically, processes and mediums are provided that provide a high level of ethanol productivity even after removing or reducing concentrations of components that were previously considered to be essential or required at certain concentration levels.

BACKGROUND

Fermentations take place in defined liquid mediums. These mediums will typically include various macro- and micro-nutrient sources that are important in improving fermentation performance. Mediums used in connection with less common substrates, such as gaseous substrates, require well defined mediums to optimize performance. Anaerobic fermentations also require well defined mediums.

Anaerobic microorganisms can produce ethanol from carbon monoxide (CO) through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlii* ATCC No. 55988 and 55989.

U.S. Pat. No. 7,285,402 describes mediums known for use in anaerobic fermentation of gaseous substrates to produce ethanol. Various component and component concentrations in the medium are effective for providing high levels of ethanol productivity. Eliminating certain components and reducing required concentrations levels of other components while maintaining ethanol productivity may provide significant cost savings, especially at a commercial scale fermentation.

SUMMARY

A process for fermenting syngas and a fermentation medium provides high ethanol productivity while removing medium components that were previously thought to be essential. Removal of certain medium components and reducing concentrations of other medium components provides significant operational cost savings at a commercial scale.

In one aspect, a fermentation process includes fermenting syngas in a fermentation medium. The process is effective for providing a specific STY of at least about 1 g ethanol/(L·day·gram cells). In this aspect, the fermentation medium has less than about 1.04 ppm boron, less than about 0.16 ppm manganese, less than about 0.26 ppm molybdenum, or less than about 0.16 ppm copper.

In another aspect, a fermentation medium includes at least about 112 mg of nitrogen per gram of cells produced, at least about 10.5 mg of phosphorous per gram of cells produced, or at least about 26 mg of potassium per gram of cells produced. In another aspect, the fermentation medium has less than about 1.04 ppm boron, less than about 0.16 ppm manganese, less than about 0.26 ppm molybdenum, or less than about 0.16 ppm copper.

In another aspect, a fermentation process includes fermenting syngas in a fermentation medium. The process effective for providing a specific STY of at least about 1 gram of ethanol/(L·day·gram cells). The fermentation medium has a weight ratio of $NH_4^+$ to B of about 625:1 or more, or a weight ratio of $NH_4^+$ to Mn of about 4050:1 or more, or a weight ratio of $NH_4^+$ to Mo of about 2500:1 or more, or a ratio of $NH_4^+$ to Cu of about 4050:1 or more; or the fermentation medium has a weight ratio of P to B of about 30:1 or more, or a weight ratio of P to Mn of about 190:1 or more, or a weight ratio of P to Mo of about 120:1 or more, or a weight ratio of Mn to Cu of about 190:1 or more; or the fermentation medium has a weight ratio of K to B of about 35:1 or more, or a weight ratio of K to Mn of about 245:1 or more, or a weight ratio of K to Mo of about 150:1 or more, or a weight ratio of K to Cu of about 245:1 or more.

DETAILED DESCRIPTION

The following description is not to be taken in a limiting sense, but is made merely for the purpose of describing the general principles of exemplary aspects. The scope of the invention should be determined with reference to the claims.

A process and medium composition are provided that surprisingly and unexpectedly provides a high level of ethanol productivity even after removing or reducing concentrations of one or more components that were previously thought to be essential or required at certain concentration levels. In this aspect, the medium may have reduced concentration levels of one or more nutrients that include B, Mn, Mo, and Cu. Nutrient concentrations in the medium may be as follows:

B: less than about 1.04 ppm B, in another aspect, less than about 1.0 ppm B, in another aspect, less than about 0.75 ppm B, in another aspect, less than about 0.5 ppm B, and in another aspect, less than about 0.025 ppm B;

Mn: less than about 0.16 ppm Mn, in another aspect, less than about 0.15 ppm Mn, in another aspect, less than about 0.10 ppm Mn, in another aspect, less than about 0.05 ppm Mn, and in another aspect, less than about 0.0025 ppm Mn;

Mo: less than about 0.26 ppm Mo, in another aspect, less than about 0.25 ppm Mo, in another aspect, less than about 0.20 ppm Mo, in another aspect, less than about 0.10 ppm Mo, and in another aspect, less than about 0.001 ppm Mo; or Cu: less than about 0.16 ppm Cu, in another aspect, less than about 0.15 ppm Cu, in another aspect, less than about 0.10 ppm Cu, in another aspect, less than about 0.05 ppm Cu, and in another aspect, less than about 0.01 ppm Cu.

In another aspect, weight ratios may be as follows:

$NH_4^+$ to B: about 625:1 or more, in another aspect, about 650:1 or more, in another aspect, about 675:1 or more, in another aspect, about 700:1 or more, in another aspect, about 750:1 or more, and in another aspect, about 800:1 or more; or $NH_4^+$ to Mn: about 4050:1 or more, in another aspect, about 4100:1 or more, in another aspect, about 4200:1 or more, in another aspect, about 4300:1 or more, in another aspect, about 4400:1 or more, and in another aspect, about 4500:1 or more; or $NH_4^+$ to Mo: about 2500:1 or more, in another aspect, about 2600:1 or more, in another aspect, about 2700:1 or more, in another aspect, about 2800:1 or more, in another aspect, about 2900:1 or more, and in another aspect, about 3000:1 or more; or $NH_4^+$ to Cu: about 4050:1 or more; in another aspect, about 4100:1 or more, in another aspect, about 4200:1 or more, in another aspect, about 4300:1 or more, in another aspect, about 4400:1 or more, and in another aspect, about 4500:1 or more; or P to B: about 30:1 or more, in another aspect, about 35:1 or more, in another aspect, about 40:1 or more, in another aspect, about 45:1 or more, in another aspect, about 50:1 or more, and in another aspect, about 100:1 or more; or P to Mn: about 190:1 or more, in another aspect, about 200:1 or more, in another aspect, about 225:1 or more, in another aspect, about 250:1 or more, in another aspect, about 275:1 or more, and in another aspect, about 300:1 or more; or P to Mo: about 120:1 or more, in another aspect, about 130:1 or more, in another aspect, about 140:1 or more, in another aspect, about 150:1 or more, in another aspect, about 175:1 or more, and in another aspect, about 200:1 or more; or P to Cu: about 190:1 or more; in another aspect, about 200:1 or more, in another aspect, about 225:1 or more, in another aspect, about 250:1 or more, in another aspect, about 275:1 or more, and in another aspect, about 300:1 or more; or K to B: about 35:1 or more, in another aspect, about 40:1 or more, in another aspect, about 45:1 or more, in another aspect, about 50:1 or more, in another aspect, about 75:1 or more, and in another aspect, about 100:1 or more; or K to Mn: about 245:1 or more, in another aspect, about 250:1 or more, in another aspect, about 260:1 or more, in another aspect, about 270:1 or more, in another aspect, about 280:1 or more, and in another aspect, about 300:1 or more; or K to Mo: about 150:1 or more, in another aspect, about 250:1 or more, in another aspect, about 260:1 or more, in another aspect, about 270:1 or more, in another aspect, about 280:1 or more, and in another aspect, about 300:1 or more; or K to Cu: about 245:1 or more, in another aspect, about 250:1 or more, in another aspect, about 260:1 or more, in another aspect, about 270:1 or more, in another aspect, about 280:1 or more, and in another aspect, about 300:1 or more.

Definitions

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is combustible and is often used as a fuel source or as an intermediate for the production of other chemicals.

The terms "fermentation", fermentation process" or "fermentation reaction" and the like are intended to encompass both the growth phase and product biosynthesis phase of the process. In one aspect, fermentation refers to conversion of CO to alcohol.

The term "cell density" means mass of microorganism cells per unit volume of fermentation broth, for example, grams/liter. In this aspect, the process and mediums are effective for providing a cell density of at least about 1.0 g/L. Cell density may be from about 1 to about 25 g/L, in another aspect, about 1 to about 20 g/L, in another aspect, about 1 to about 10 g/L, in another aspect, about 2 to about 8 g/L, in another aspect, about 3 to about 6 g/L, and in another aspect, about 4 to about 5 g/L.

The term "cell recycle" refers to separation of microbial cells from a fermentation broth and returning all or part of those separated microbial cells back to the fermentor. Generally, a filtration device is used to accomplish separations.

Medium Composition

The processes and mediums described herein are effective for providing a high level of productivity. In this aspect, the process is effective for providing a specific STY (specific space time yield expressed as g ethanol/(L·day·gram cells) of at least about 1, in another aspect, about 1 to about 10, in another aspect, about 2 to about 8, in another aspect, about 3 to about 7, and in another aspect, about 4 to about 6.

In a related aspect, productivity may be expressed as STY (space time yield expressed as g ethanol/(L·day). In this aspect, the process is effective for providing a STY (space time yield) of at least about 10 g ethanol/(L·day). Possible STY values include about 10 g ethanol/(L·day) to about 200 g ethanol/(L·day), in another aspect, about 10 g ethanol/(L·day) to about 160 g ethanol/(L·day), in another aspect, about 10 g ethanol/(L·day) to about 120 g ethanol/(L·day), in another aspect, about 10 g ethanol/(L·day) to about 80 g ethanol/(L·day), in another aspect, about 20 g ethanol/(L·day) to about 140 g ethanol/(L·day), in another aspect, about 20 g ethanol/(L·day) to about 100 g ethanol/(L·day), in another aspect, about 40 g ethanol/(L·day) to about 140 g ethanol/(L·day), and in another aspect, about 40 g ethanol/(L·day) to about 100 g ethanol/(L·day).

In another aspect, the process and mediums are effective for providing a CO conversion of at least about 5% to about 99%, in another aspect, about 10% to about 90%, in another aspect, about 20% to about 80%, in another aspect, about 30% to about 70%, and in another aspect, about 40% to about 90%.

In one aspect, the medium includes at least one or more of a nitrogen source, at least one or more phosphorous source and at least one or more of a potassium source. The medium may include any one of the three, any combination of the three, and in an important aspect, includes all three. A nitrogen source may include a nitrogen source selected from the group consisting of ammonium chloride, ammonium phosphate, ammonium sulfate, ammonium nitrate, and mixtures thereof. A phosphorous source may include a phosphorous source selected from the group consisting of phosphoric acid, ammonium phosphate, potassium phosphate, and mixtures thereof. A potassium source may include a potassium source selected from the group consisting of potassium chloride, potassium phosphate, potassium nitrate, potassium sulfate, and mixtures thereof.

In one aspect, the medium includes one or more of iron, tungsten, nickel, cobalt, magnesium, sulfur and thiamine. The medium may include any one of these components, any combination, and in an important aspect, includes all of these components. An iron may include an iron source selected from the group consisting of ferrous chloride, ferrous sulfate, and mixtures thereof. A tungsten source may include a tungsten source selected from the group consisting of sodium tungstate, calcium tungstate, potassium tungstate, and mixtures thereof. A nickel source may include a nickel source selected from the group consisting of nickel chloride, nickel sulfate, nickel nitrate, and mixtures thereof. A cobalt source may include a cobalt source selected from the group consisting of cobalt chloride, cobalt fluoride, cobalt bromide, cobalt iodide and mixtures thereof. A magnesium source may include a magnesium source selected from the group consisting of magnesium chloride, magnesium sulfate, magnesium phosphate, and mixtures thereof. A sulfur source may include cysteine, sodium sulfide, and mixtures thereof.

Concentrations of various components are as follows:

| Component | Concentration Range (expressed as mg or µg nutrient per gram of cells) | Preferred Range (expressed as mg or µg nutrient per gram of cells) |
| --- | --- | --- |
| nitrogen (N) | 112-160 mg | 140-150 mg |
| phosphorus (P) | 10.5-15 mg | 12-13 mg |
| potassium (K) | 26-36 mg | 28-33 mg |
| iron (Fe) | 2.7-5 mg | 3.0-4.0 mg |
| tungsten (W) | 10-30 µg | 15-25 µg |
| Nickel (Ni) | 34-40 µg | 35-37 µg |
| Cobalt (Co) | 9-30 µg | 15-20 µg |
| Magnesium (Mg) | 4.5-10 mg | 5-7 mg |
| Sulfur (S) | 11-20 mg | 12-16 mg |
| Thiamine | 6.5-20 µg | 7-12 µg |

Process operation maintains a pH in a range of about 4.2 to about 4.8. The medium includes less than about 0.01 g/L yeast extract and less than about 0.01 g/L carbohydrates.

Syngas

Syngas may be provided from any know source. In one aspect, syngas may be sourced from gasification of carbonaceous materials. Gasification involves partial combustion of biomass in a restricted supply of oxygen. The resultant gas mainly includes CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. The syngas will have a $CO/CO_2$ ratio of at least about 0.75, in another aspect, at least about 1.0, and in another aspect, at least about 1.5. Some examples of suitable gasification methods and apparatus are provided in U.S. Ser. Nos. 13/427,144, 13/427,193 and 13/427,247, all of which were filed on Mar. 22, 2012, and all of which are incorporated herein by reference.

In another aspect, syngas utilized for propagating acetogenic bacteria may be substantially CO. As used herein, "substantially CO" means at least about 50 mole % CO, in another aspect, at least about 60 mole % CO, in another aspect, at least about 70 mole % CO, in another aspect, at least about 80 mole % CO, and in another aspect, at least about 90 mole % CO.

Bioreactor Operation

In accordance with one aspect, the fermentation process is started by addition of medium to the reactor vessel. The medium is sterilized to remove undesirable microorganisms and the reactor is inoculated with the desired microorganisms. In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui*, *Acetoanaerobium noterae*, *Acetobacterium woodii*, *Alkalibaculum bacchi* CP11 (ATCC BAA-1772), *Blautia producta*, *Butyribacterium methylotrophicum*, *Caldanaerobacter subterraneous*, *Caldanaerobacter subterraneous pacificus*, *Carboxydothermus hydrogenoformans*, *Clostridium aceticum*, *Clostridium acetobutylicum*, *Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei*, *Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* O-52 (ATCC 55889), *Clostridium magnum*, *Clostridium pasteurianum* (DSM 525 of DSMZ Germany), *Clostridium ragsdali* P11 (ATCC BAA-622), *Clostridium scatologenes*, *Clostridium thermoaceticum*, *Clostridium ultunense*, *Desulfotomaculum kuznetsovii*, *Eubacterium limosum*, *Geobacter sulfurreducens*, *Methanosarcina acetivorans*, *Methanosarcina barkeri*, *Morrella thermoacetica*, *Morrella thermoautotrophica*, *Oxobacter pfennigii*, *Peptostreptococcus productus*, *Ruminococcus productus*, *Thermoanaerobacter kivui*, and mixtures thereof.

Upon inoculation, an initial feed gas supply rate is established effective for supplying the initial population of microorganisms. Effluent gas is analyzed to determine the content of the effluent gas. Results of gas analysis are used to control feed gas rates. Upon reaching desired levels, liquid phase and cellular material is withdrawn from the reactor and replenished with medium. In this aspect, the bioreactor is operated to maintain a cell density of at least about 2 grams/liter, and in another aspect, about 2 to about 50 grams/liter, in various other aspects, about 5 to about 40 grams/liter, about 5 to about 30 grams/liter, about 5 to about 20 grams/liter, about 5 to about 15 grams/liter, about 10 to about 40 grams/liter, about 10 to about 30 grams/liter, about 10 to about 20 grams/liter, and about 10 to about 15 grams/liter. Cell density may be controlled through a recycle filter. A further description of bioreactor operation is set forth in U.S. Provisional Application Nos. 61/571,564, filed Jun. 30, 2011, U.S. Provisional Application No. 61/571,565, filed Jun. 30, 2011, and in U.S. Provisional Application No. 61/573,845, filed Sep. 13, 2011, all of which are incorporated herein by reference.

EXAMPLES

Example 1: Fermentation with Boron, Copper and Manganese Limitations

Experiments were conducted in a bioreactor (New Brunswick BioFlo I or IIc) operated as a straight through CSTR, with no permeate purge. Bioreactor operating conditions were as follows:

Culture type was *Clostridium ljungdahlii* C01.
Culture temperature was kept at 38-39° C.
Agitation was 850 rpm on an analog readout.
The unroused culture volume was ~1600-1650 ml. The culture pH set point was 4.5. A solution of 7.7% $NaHCO_3$ was used for pH control.

Feed gas was a synthetic blend of 15% $H_2$, 45% $N_2$, 30% CO and 10% $CO_2$ fed to the culture at a rate of 282 ml/min.

Medium was fed into the reactor at ~0.88 ml/min, or ~1300 ml/day.

Liquid and cell retention times were approximately 29-31 hours.

The starting medium used was as described below.

| Component/Ion | Added As | Conc in Med (ppm) |
|---|---|---|
| $NH_4^+$ | $NH_4Cl/(NH_4)_2HPO_4$ | 838 |
| Fe | $FeCl_2 \cdot 4H_2O$ | 16.8 |
| Ni | $NiCl_2 \cdot 6H_2O$ | 0.1975 |
| Co | $CoCl_2 \cdot 6H_2O$ | 0.991 |
| Se | $Na_2SeO_3$ | 0.0913 |
| Zn | $ZnSO_4 \cdot 7H_2O$ | 0.455 |
| Mo | $Na_2MoO_4 \cdot 2H_2O$ | 0.238 |
| Mn | $MnCl_2 \cdot 4H_2O$ | 0.167 |
| B | $H_3BO_3$ | 1.05 |
| Cu | $CuCl_2 \cdot 2H_2O$ | 0.149 |
| W | $Na_2WO_4 \cdot 2H_2O$ | 1.12 |
| K | KCl | 78.6 |
| Mg | $MgCl_2 \cdot 6H_2O$ | 59.8 |
| Na | NaCl | 78.7* |
| Ca | $CaCl_2 \cdot 2H_2O$ | 54.5** |
| Cysteine HCl | Cysteine HCl | 250 |
| P | $H_3PO_4/(NH_4)_2HPO_4$ | 279 |

*$Na^+$ concentration is from NaCl only. It does not include $Na^+$ from the other components such as $Na_2WO_4 \cdot 2H_2O$.
**$Ca^{+2}$ concentration does not include calcium from pantothenic acid, calcium salt as other sources provide only trace or insignificant amounts of calcium.

The bioreactor was operated until the culture obtained a high productivity steady state. High productivity steady state was defined as ~2.5-3 g/L cell density, an ethanol concentration of >20 g/L, a CO uptake of >3.0 mmol/min, and a hydrogen uptake of >0.5 mmol/min. In the process of obtaining a high productivity steady state, the concentration of $CaCl_2 \cdot 2H_2O$ was reduced to zero and ammonium concentration was lowered to 546 ppm.

Once the culture was at a high productivity steady state, the B, Mn and Cu sources were eliminated from the medium preparation. Just prior to removing those components, the culture conditions/parameters were as follows:

Cell density—2.9 g/L
CO Conversion—86%
$H_2$ Conversion—32%
CO Uptake—3.0 mmol/min
$H_2$ Uptake—0.54 mmol/min
Ethanol—21.8 g/L
Total Acetyl—2.7 g/L
Butanol—0.35 g/L The culture parameters of gas uptake, $H_2$ and CO, product concentrations and cell density were then monitored for any adverse affects. If removing B, Cu and Mn did not affect those parameters after several (>3) cell retention times they were considered to be unnecessary to the culture After ~5.7 cell retention times (170 hours) the boron, copper and manganese concentration in the culture broth had dropped to ~0.41% of the beginning concentrations (0.0043 ppm B, 0.0006 ppm Cu, and 0.0068 ppm Mn down from 1.05 ppm B, 0.149 ppm Cu and 1.67 ppm Mn). The estimated remaining component concentrations in the broth were determined by washout calculations using a starting calcium concentration, MFR, LRT and any additions of those components through either the medium or spikes into the bioreactor. There were no adverse affects on culture performance.

After 170 hours with no boron, copper and manganese addition, the culture parameters/condition were as follows:

Cell density—2.9 g/L
CO Conversion—86%
$H_2$ Conversion—36%
CO Uptake—3.0 mmol/min
$H_2$ Uptake—0.61 mmol/min
Ethanol—21.0 g/L
Total Acetyl—2.9 g/L
Butanol—0.32 g/L

Example 2: Fermentation with Cobalt Limitations

Experiments were conducted in a bioreactor (New Brunswick BioFlo I or IIc) operated as a straight through CSTR, with no cell recycle loop. Bioreactor operating conditions were as follows:

Culture type was *Clostridium ljungdahlii* C01.
Culture temperature was kept at 37-39° C.
Agitation was 850 rpm on an analog readout (actual agitation was 931 rpm based on a tachometer calibration curve).
The unroused culture volume was ~1600-1650 ml.
Roused culture volume was ~1950 ml.
The culture pH set point was 4.5. A solution of 7.7% $NaHCO_3$ was used for pH control.

Feed gas was a synthetic blend of 15% $H_2$, 45% $N_2$, 30% CO and 10% $CO_2$ fed to the culture at a rate of 286 ml/min.

Medium was fed into the reactor at ~0.83 to ~0.86 ml/min, or ~1220 ml/day.

Liquid and cell retention times were approximately 31-33 hours.

The medium used was as described below.

| Component/Ion | Added As | Conc in Med (ppm) |
|---|---|---|
| $NH_4^+$ | $NH_4Cl/(NH_4)_2HPO_4$ | 654 |
| Fe | $FeCl_2 \cdot 4H_2O$ | 16.8 |
| Ni | $NiCl_2 \cdot 6H_2O$ | 0.198 |

-continued

| Component/Ion | Added As | Conc in Med (ppm) |
|---|---|---|
| Co | $CoCl_2 \cdot 6H_2O$ | 0-0.198 |
| Se | $Na_2SeO_3$ | 0.012 |
| Zn | $ZnSO_4 \cdot 7H_2O$ | 0 |
| Mo | $Na_2MoO_4 \cdot 2H_2O$ | 0 |
| Mn | $MnCl_2 \cdot 4H_2O$ | 0 |
| B | $H_3BO_3$ | 0 |
| Cu | $CuCl_2 \cdot 2H_2O$ | 0 |
| W | $Na_2WO_4 \cdot 2H_2O$ | 1.12 |
| K | KCl | 78.7 |
| Mg | $MgCl_2 \cdot 6H_2O$ | 14.8 |
| Na | NaCl | 0* |
| Ca | $CaCl_2 \cdot 2H_2O$ | 0 |
| Cysteine HCl | Cysteine HCl | 250 |
| $PO_4^{-2}$ | $H_3PO_4/(NH_4)_2HPO_4$ | 384 |
| Pantothenic Acid | Pantothenic Acid | 0.0404 |
| Biotin | Biotin | 0.032 |
| Thiamin | Thiamine | 0.080 |

*$Na^+$ concentration is from NaCl only. It does not include $Na^+$ from the other components such as $Na_2WO_4 \cdot 2H_2O$.

The bioreactor was operated until the culture obtained a high productivity steady state. High productivity steady state was defined as ~2.5-3 g/L cell density, an ethanol concentration of >20 g/L, a CO uptake of >3.0 mmol/min, and a hydrogen uptake of >0.5 mmol/min.

The culture parameters of gas uptake, $H_2$ and CO, product concentrations and cell density were then monitored for any adverse affects. If the reduction in the component concentration did not affect those parameters after several (>3) cell retention times, the concentration would be reduced further. If after a reduction in a component's concentration a drop in the culture parameters was seen, the concentration would be increased back to a level that had previously shown to be adequate. If the culture recovered, the concentration would be lowered again, sometimes to the same level as before to repeat the effect, sometime to a level somewhere in between what worked and what caused problems.

At the beginning of the experiment the cobalt concentration was at normal medium levels, or 0.991 ppm. Culture parameters were stable at ~3 g/L cell density; 22-26 g/L ethanol; 2.7-3.7 g/L acetyl; 3.1 mmol/min CO uptake; and 0.5-0.7 mmol/min H2 uptake. The cobalt was removed from the medium starting at t=0 hours. As the cobalt was washing out of the fermentor, there was only a slight drop in CO uptake from 3.1 to 2.9 mmol/min. All other parameters remained more or less constant until t=121 hrs. At that time the $H_2$ and CO uptake dropped to 0.16 and 2.6 mmol/min respectively. The total acetyl also dropped quickly at that time to 0.77 g/L indicating that the cobalt concentration had dropped to or below a limiting level. Cobalt washout calculations showed that by the time the low cobalt level was affecting the culture parameters, the cobalt concentration in the reactor had dropped to 0.0222 ppm, or 2.24% of the original concentration. Cobalt was added into the reactor only, to raise the concentration to 23.3% of normal levels, or 0.231 ppm. The effect was immediately seen as an increase in CO uptake, $H_2$ uptake and acid concentration. No cobalt was added back into the medium at this time to let the cobalt in the reactor to wash back down to limiting levels once more. As seen previously, the culture parameters continued to show no signs of distress until the cobalt had washed below 0.0220 ppm. At t=210 hrs, the $H_2$ and CO uptakes as well as the acid concentration had all dropped once again, showing the effects of cobalt limitation. This time cobalt was added back to the reactor and medium at 20% (0.198 ppm) in the medium and 21.2% (0.21 ppm) in the reactor. As before, the effect was an immediate increase in both gas uptakes and in acid concentration.

The two different times the cobalt was washed out of the reactor until the culture showed signs of distress resulted in a cobalt concentration of ~0.022 ppm as limiting to the culture. When the cobalt concentration was then set at 0.023 ppm, the culture performed well with no adverse effects. Based on that cobalt concentration the calculated parameters used to better correlate nutrient addition verses culture performance were as follows: The mg of cobalt added per mmol of gas uptake was 0.005 (mg/mmol). The μg of cobalt added per gram of cells produced was ~9 (μg/g).

Recovery from a cobalt limitation was rapid with no lasting adverse effects. No permanent harm was done to the culture if cobalt was increased before the parameters drop to the point of secondary problems, i.e. gas toxicity or no acid present.

Dropping cobalt levels did cause the cell concentration to drop. There was no clear correlation between cobalt limitation and butanol production. Both CO and H2 conversion/uptake were affected by cobalt limitation, but there was little to no effect seen until the cobalt concentration in the culture dropped to ~0.022 ppm or lower. There was no gradual drop in gas conversion. However, once the cobalt concentration dropped past the limitation point both CO and $H_2$ conversions dropped very quickly. Once the CO and $H_2$ conversions began to drop, the culture was already past the critical cobalt concentration, and cobalt must be added quickly in order to recover the culture. An earlier indicator of cobalt limitation was the shift from acid to ethanol in the product ratio. The acid concentration began to drop and the ethanol concentration began to increase even before the dropping gas conversions were seen.

Example 3: Fermentation with Nickel Limitations

Experiments were conducted in a bioreactor (New Brunswick BioFlo I or IIc) operated as a straight through CSTR, with no permeate purge. Bioreactor operating conditions were as follows:

Culture type was *Clostridium ljungdahlii* C01.
Culture temperature was kept at 37-39° C.
Agitation was 700 rpm on an analog readout.
The unroused culture volume was ~1500-1650 ml.
Roused culture volume was ~1900 ml.
The culture pH set point was 4.5. A solution of 7.7% $NaHCO_3$ was used for pH control.
Feed gas was a synthetic blend of 15% $H_2$, 45% $N_2$, 30% CO and 10% $CO_2$ fed to the culture at a rate of 290 ml/min.
Medium was fed into the reactor at ~0.86 to ~0.88 ml/min, or ~1250 ml/day.
Liquid and cell retention times were approximately 27-31 hours.
The medium used was as described below.

| Component/Ion | Added As | Conc in Med (ppm) |
|---|---|---|
| $NH_4^+$ | $NH_4Cl/(NH_4)_2HPO_4$ | 655 |
| Fe | $FeCl_2 \cdot 4H_2O$ | 8.4 |
| Ni | $NiCl_2 \cdot 6H_2O$ | 0.0198-0.099 |
| Co | $CoCl_2 \cdot 6H_2O$ | 0.0991 |
| Se | $Na_2SeO_3$ | 0.0116 |
| Zn | $ZnSO_4 \cdot 7H_2O$ | 0 |
| Mo | $Na_2MoO_4 \cdot 2H_2O$ | 0 |

-continued

| Component/Ion | Added As | Conc in Med (ppm) |
|---|---|---|
| Mn | $MnCl_2 \cdot 4H_2O$ | 0 |
| B | $H_3BO_3$ | 0 |
| Cu | $CuCl_2 \cdot 2H_2O$ | 0 |
| W | $Na_2WO_4 \cdot 2H_2O$ | 1.12 |
| K | KCl | 78.7 |
| Mg | $MgCl_2 \cdot 6H_2O$ | 14.8 |
| Na | NaCl | 0* |
| Ca | $CaCl_2 \cdot 2H_2O$ | 0** |
| Cysteine HCl | Cysteine HCl | 250 |
| P | $H_3PO_4/(NH_4)_2HPO_4$ | 31.8 |
| Pantothenic Acid | Pantothenic Acid | 0.01515 |
| Biotin | Biotin | 0.0120 |
| Thiamin | Thiamine | 0.0300 |

*$Na^+$ concentration is from NaCl only. It does not include $Na^+$ from the other components such as $Na_2WO_4 \cdot 2H_2O$.
**$Ca^{+2}$ concentration does not include calcium from pantothenic acid, calcium salt.

The bioreactor was operated until the culture obtained a high productivity steady state. High productivity steady state was defined as ~2.5-3 g/L cell density, an ethanol concentration of >20 g/L, a CO uptake of >3.0 mmol/min, and a hydrogen uptake of >0.5 mmol/min.

The culture parameters of gas uptake, $H_2$ and CO, product concentrations and cell density were then monitored for any adverse affects. If the reduction in the component concentration did not affect those parameters after several (>3) cell retention times, the concentration would be reduced further. If after a reduction in a component's concentration a drop in the culture parameters was seen, the concentration would be increased back to a level that had previously shown to be adequate. If the culture recovered, the concentration would be lowered again, sometimes to the same level as before to repeat the effect, sometime to a level somewhere in between what worked and what caused problems.

At the start of this experiment the Ni concentration in the reactor had dropped to 56% of the original Ni level, or 0.11 ppm. Nickel concentrations in the reactor were based on "washout" calculations that used Ni concentration in the medium, Ni additions to the medium and/or reactor, and the liquid flows through the system to calculate the changing Ni concentration in the reactor with time. As the Ni continued to wash out of the reactor the culture parameters did not change. Cell density remained ~2.8 g/L; CO uptake was ~3.2 mmol/min; $H_2$ uptake was ~0.7 mmol/min; ethanol concentration was 24 g/L; and the total acetyl level was ~2.5 g/L. However, by about t=107 hours the cell morphology had started to worsen. The percentage of long cells had increased from ~5% to 5-10% and the length of the long cells was increasing. The long cells were now showing some warping. The overall length of the average cells was also increasing but with only mild or no warping. The Ni concentration in the reactor had dropped to 0.0996 ppm around the time the cell morphology declined.

The nickel concentration in the reactor washed out to 50%, 0.0988 ppm, by t=~160 hrs. As before, the culture parameters did not vary much. However, the cell morphology was worse when observed around t=250 hrs. The percentage of long cells had increased to 10-20% along with the degree of bending or warping of those long cells. The remainder of the culture was average to slightly long in length with occasional mild bending. There were no severely bent cells, like coils or springs, but there were several grainy cells and hollow bodied cells seen. Again, no change to the culture parameters or nickel concentration was made.

The nickel concentration in the reactor remained at 50%, or 0.0988 ppm, until t=1885 hours. With a medium flow rate of ~0.87 ml/min, the nickel feed rate was 0.12 mg/day. Culture parameters were fairly constant at ~2.8 g/L cell density, ~3.2 mmol/min CO uptake, ~0.7 mmol/min $H_2$ uptake, ~25 g/L ethanol, ~2.5 g/L total acetyl, and ~0.3 g/L butanol. At the 50% nickel feed rate, Ni was added at ~34 µg per gram of cells produced, 0.022 µg per mmol of gas uptake. The cell morphology did not continue to worsen once the Ni concentration was 0.0988 ppm. It remained ~10% long cells with mild warping, ~5% very long cells with moderate warping, and the remainder of the cells was average to slightly long in length with occasional warping.

At t=445 hrs, the Ni concentration in the medium was reduced to 25% of the original, or 0.049 ppm. Almost immediately a slow but steady change to the culture parameters was observed. The CO uptake remained constant at ~3.2 mmol/min, but the $H_2$ uptake started to decrease from 0.7-0.8 mmol/min to 0.6-0.7 mmol/min within ~120 hours of the Ni reduction. The ethanol concentration started to drop from ~24 g/L to ~21 g/L, and the total acetyl level also started to drop from ~2.5 g/L to ~2.0 g/L within ~160 hours of the Ni change. The butanol concentration started a slow but steady increase almost as soon as the Ni was lowered to the medium. The concentration had increased from ~0.21 g/L to ~0.34 g/L by ~635 hours after Ni was lowered. The cell morphology was relatively unchanged. The lower Ni feed rate was now 0.062 mg/day. At that feed rate Ni was added at ~18 µg per gram of cells produced, ~0.011 µg per mmol of gas uptake.

To speed the effect of a low Ni concentration on the culture, the Ni level in the medium was dropped to 10% or the original concentration, or 0.0198 ppm, at t=638 hrs. The same trends in the culture parameters continued as before but at a faster rate. The $H_2$ uptake and acid concentration continued to decrease. The cell density and CO uptake did not change, and the butanol concentration continued to rise. There was still no change in cell density as it remained ~2.8 g/L. Hydrogen uptake was ~0.5-0.6 mmol/min. Carbon monoxide uptake was still ~3.2 mmol/min. The product concentrations were ~21 g/L ethanol, ~1.5 g/L total acetyl, and ~0.65 g/L butanol. The Ni concentration was kept at 10% for an additional 86 hours to determine a longer term affect on parameters and cell morphology. There was no further decline in culture parameters. Culture morphology did worsen somewhat showing an increase in the number of long cells as well as an increase in the overall length of the cells. Approximately 10-15% of the cells were classified as long with warping. The remainder of the cells was short to slight long with the majority of the cells an average length and no warping. With the 10%, or 0.01975 ppm, Ni concentration in the medium, the Ni feed rate was 0.025 mg/day. This provided ~7 µg of Ni added per gram of cells produced, or ~0.0048 µg of Ni added per mmol of gas uptake. At t=2270 hours, the nickel concentration was increased back to 50%, or 0.0988 ppm. Hydrogen uptake increased to ~0.7 mmol/min. The CO uptake remained ~3.2 mmol/min. Ethanol rose to ~24 g/L. Acid increased to ~2.5 g/L. Butanol dropped to ~0.24 g/L, and the cell density remained unchanged at ~2.9 g/L. Cell morphology also improved showing an overall decrease in the length of cells as well as the number of long cells. Approximately 5-10% of the cells were classified as long with mild warping. The rest of the cells were short to slightly long in length with most of them an average length with only occasional mild warping.

Decreasing the Ni concentration in the reactor to 0.0988 ppm, or 50%, caused no discernable change in the culture parameters. However, the cell morphology did worsen showing an increase in the overall length of the culture where up to 20% of the cells were considered long with mild to moderate warping. The cell morphology did not continue to worsen while at 50% Ni concentration showing that the culture would hold at steady state under that condition.

When the nickel concentration in the medium was dropped to 25% of normal, or 0.049 ppm, the ethanol and total acetyl concentration and the $H_2$ uptake all started to drop. At the same time, the butanol concentration started to increase slowly. These were all indications that the culture was Ni limited, but the cell morphology remained relatively unchanged.

Based on the calculated nickel concentration in the reactor as the culture parameters and cell morphology started to decline, the morphology was the first to worsen as the Ni washed out down to 50%, or 0.099 ppm. As the Ni concentration dropped further to 36%, or 0.072 ppm, the butanol concentration worsened. At 29% Ni, or 0.057 ppm, the $H_2$ uptake started to drop. Then finally at 25% Ni, or 0.050 ppm, the ethanol and acid concentrations started to decline. At 50% Ni only the culture morphology was affected. Once the Ni level dropped further, culture uptake and productivity declined. This signifies that a 50% Ni concentration in the medium, or a 0.12 mg/day feed rate, was very close to the Ni limitation. Based on the culture parameters and the 0.12 mg/day Ni feed rate, the Ni was added at ~34 µg per gram of cells produced, ~0.022 µg per mmol of gas uptake.

Signs of Ni limitation were decreased $H_2$ uptake, decreased acid level, and increased butanol followed by a decreased ethanol concentration. There was no change in cell density seen. Eventually cell morphology was affected showing an increase in the total number of long cells and the overall length of those long cells. In general, as the length of the cells increased, the cell becomes more bent or warped.

Example 4: Fermentation with Tungsten Limitations

Experiments were conducted in a bioreactor (New Brunswick BioFlo I or IIc) operated as a straight through CSTR, with no permeate purge. Bioreactor operating conditions were as follows:

Culture type was *Clostridium ljungdahlii* C01.
Culture temperature was kept at 38-39° C.
Agitation was 700 rpm on an analog readout.
The unroused culture volume was ~1550-1700 ml.
Roused culture volume was ~1900 ml.
The culture pH set point was 4.5. A solution of 7.7% $NaHCO_3$ was used for pH control.
Feed gas was a synthetic blend of 15% $H_2$, 45% $N_2$, 30% CO and 10% $CO_2$ fed to the culture at a rate of 290 ml/min.
Medium was fed into the reactor at ~0.86 to ~0.88 ml/min, or ~1250 ml/day.
Liquid and cell retention times were approximately 28-31 hours.
The medium used was as described below.

| Component/Ion | Added As | Conc in Med (ppm) |
|---|---|---|
| $NH_4^+$ | $NH_4Cl/(NH_4)_2HPO_4$ | 655 |
| Fe | $FeCl_2 \cdot 4H_2O$ | 8.4 |
| Ni | $NiCl_2 \cdot 6H_2O$ | 0.099-0.118 |
| Co | $CoCl_2 \cdot 6H_2O$ | 0.0991 |
| Se | $Na_2SeO_3$ | 0.0116 |
| Zn | $ZnSO_4 \cdot 7H_2O$ | 0 |
| Mo | $Na_2MoO_4 \cdot 2H_2O$ | 0 |
| Mn | $MnCl_2 \cdot 4H_2O$ | 0 |
| B | $H_3BO_3$ | 0 |
| Cu | $CuCl_2 \cdot 2H_2O$ | 0 |
| W | $Na_2WO_4 \cdot 2H_2O$ | 0-0.56 |
| K | KCl | 78.7 |
| Mg | $MgCl_2 \cdot 6H_2O$ | 14.8 |
| Na | NaCl | 0* |
| Ca | $CaCl_2 \cdot 2H_2O$ | 0** |
| Cysteine HCl | Cysteine HCl | 250 |
| P | $H_3PO_4/(NH_4)_2HPO_4$ | 31.8-60 |
| Pantothenic Acid | Pantothenic Acid | 0.01515 |
| Biotin | Biotin | 0.0120 |
| Thiamin | Thiamine | 0.0300 |

*$Na^+$ concentration is from NaCl only. It does not include $Na^+$ from the other components such as $Na_2WO_4 \cdot 2H_2O$.
**$Ca^{+2}$ concentration does not include calcium from pantothenic acid, calcium salt.

The bioreactor was operated until the culture obtained a high productivity steady state. High productivity steady state was defined as ~2.5-3 g/L cell density, an ethanol concentration of >20 g/L, a CO uptake of >3.0 mmol/min, and a hydrogen uptake of >0.5 mmol/min.

The culture parameters of gas uptake, $H_2$ and CO, product concentrations and cell density were then monitored for any adverse affects. If the reduction in the component concentration did not affect those parameters after several (>3) cell retention times, the concentration would be reduced further. If after a reduction in a component's concentration a drop in the culture parameters was seen, the concentration would be increased back to a level that had previously shown to be adequate. If the culture recovered, the concentration would be lowered again, sometimes to the same level as before to repeat the effect, sometime to a level somewhere in between what worked and what caused problems.

During phosphorus testing, tungsten was removed from the medium at t=0 hours. The culture was not recovering as anticipated during the phosphorus testing despite the addition of P back into the reactor and medium preparation. When a series of attempts to improve the culture failed, as a last resort tungsten was added back to the reactor at a 50% or normal level, or 0.56 ppm, at t=812 hours by adding 8 ml of a 0.2 g/l $Na_2WO_4 \cdot 2H_2O$ solution to 1.6 liters of culture. Tungsten washout calculations showed that the tungsten level in the reactor had washed out to <0.0001 ppm. Upon addition of tungsten, the culture responded almost immediately. The $H_2$ uptake started increasing. With the improved $H_2$ conversions the feed gas flow rate was increased back to the original setting of ~290 ml/min, by t=885 hours. That increased the CO and $H_2$ uptakes back to 3.2 and ~0.75 mmol/min respectively. With the increased gas uptake the cell density increased to ~2.7 g/L, and the ethanol level rose to ~22 g/L. The total acetyl and butanol levels remained about the same at ~3.5 and ~0.45 g/L respectively. Another change in the culture was an improvement in the cell morphology. With the tungsten addition, the overall cell length dropped significantly and there was less bending and warping of the cells.

No tungsten was added back to the medium in order to wash the level in the reactor back down in order to try and determine the level of tungsten required by the culture. As the tungsten was washing out the $H_2$ uptake started to trend down around t=904 hours. No tungsten was added to either reactor or medium. Around t=981 hours the butanol concentration started to slowly increase. Then around t=1030 hours the ethanol concentration started to drop. Still no tungsten was added. By t=1100 hours $H_2$ uptake was ~0.2 mmol/min; ethanol was ~17 g/L; and butanol was ~0.74 g/L. The CO uptake had not been affected, and the cell density was about the same.

At t=1100 hours tungsten was added to the reactor at 50% of normal or 0.56 ppm. As seen before, the culture started to improve almost immediately. The $H_2$ uptake started to increase; ethanol concentration rose; the acid level dropped; cell density increased slightly; and the butanol concentration started to decrease. By the end of the reporting period the cell density was ~3.3 g/L; CO and $H_2$ uptakes were ~3.2 and ~0.75 mmol/min respectively; ethanol was 22 g/L; acid was ~2.5 g/L; and butanol was 0.52 g/L. The tungsten level in the reactor had washed back down to 0.045 ppm, or 4.0% of original concentration, by the end of the reporting period.

The tungsten limitation was about 2.7% of the original concentration previously added, or 0.030 ppm. The culture first started showing signs of distress as a decreasing $H_2$ uptake when the tungsten had washed back out of the reactor down to 0.030 ppm. At that concentration tungsten was added at 10 µg per gram of cells produced, 0.0068 µg per mmol of gas uptake.

Example 5: Fermentation with Boron, Copper, Manganese and Molybdenum Limitations A New Brunswick Bioflow Cellii Gen 115 reactor containing a medium which did not include any B, Cu, Mn or Mo (designated medium A) or a known media (designated 402 medium) which included B, Cu, Mn and Mo was inoculated with 0.39 g/L of actively growing *Clostridium ljungdahlii* CO-1 strain.

After, the inoculation the rate of agitation of the reactor was set to 800 rpm. Gas and liquid samples taken from the reactor at approximately 1 hour intervals were analyzed for consumption or production of various gas components, broth acetic acid concentration, broth ethanol concentration and the optical density of the culture. Also the composition of various gases in the syngas was measured daily and the syngas flow to the reactor was measured real time by the mass flow controller regulating syngas to the reactor. The actual gas flow was calculated using the equation obtained by calibrating the mass flow controller. Calculations were conducted to determine the necessary rate of gas flow to the reactor to maintain a constant percentage of $H_2$ uptake from the $H_2$ in the inflow gas to the reactor or in another words, in this particular experiment, rate of gas flowing into the reactor was maintain so that culture uptake of $H_2$ is 4.5% of the total molecules of gas flowing into the reactor. Then the reactor was supplied with gas at the rate calculated above (to keep the percentage of uptake of $H_2$ from the inlet to 4.5% of total gas molecules).

For all three experiments, the cell recycle system was attached to the reactor before inoculation and had media circulating through the system for the entire duration of the experiment. For the first experiment with medium A, at 2.75 hours after the inoculation (after CO conversions had reached 80% or above), media flow to the reactor was started at 1.0 ml/min and permeate was drawn out from the reactor at 1.0 ml/min. At 6.83 hours after the inoculation, the media flow to the reactor was increased to 2.0 ml/min and permeate was drawn out from the reactor at 2.0 ml/min.

For the second experiment with the 402 medium, at 1.9 hours after the inoculation (after CO gas conversions had reached 80% or above), the media flow to the reactor was started at 2.0 ml/min and permeate was drawn out from the reactor at 2.0 ml/min.

For the third experiment with medium A, at 2.0 hours after the inoculation (after CO gas conversions had reached 80% or above), the media flow to the reactor was started at 2.0 ml/min and permeate was drawn out from the reactor at 2.0 ml/min. For all three experiments, introduction of cell recycle system was applied to remove rapid build up of ethanol in the reactor.

Medium A and the 402 medium provided close to equal performances for hydrogen uptake with *C. ljungdahlii*.

Example 6: Fermentation with Molybdenum Limitations

Experiments were conducted in a bioreactor (New Brunswick BioFlo I or IIc) operated as a straight through CSTR, with no permeate purge. Bioreactor operating conditions were as follows:

Culture type was *Clostridium ljungdahlii* C01.
Culture temperature was kept at 38-39° C.
Agitation was 850 rpm on an analog readout.
The unroused culture volume was ~1600-1650 ml.
Roused culture volume was ~1900 ml.
The culture pH set point was 4.5. A solution of 7.7% $NaHCO_3$ was used for pH control.
Feed gas was a synthetic blend of 15% $H_2$, 45% $N_2$, 30% CO and 10% $CO_2$ fed to the culture at a rate of 282 ml/min.
Medium was fed into the reactor at ~0.88 ml/min, or ~1300 ml/day.
Liquid and cell retention times were approximately 29-31 hours.
The medium used was as described below.

| Component/Ion | Added As | Conc in Med (ppm) |
| --- | --- | --- |
| $NH_4^+$ | $NH_4Cl/(NH_4)_2HPO_4$ | 546 |
| Fe | $FeCl_2 \cdot 4H_2O$ | 16.8 |
| Ni | $NiCl_2 \cdot 6H_2O$ | 0.1975 |
| Co | $CoCl_2 \cdot 6H_2O$ | 0.991 |
| Se | $Na_2SeO_3$ | 0.0456 |
| Zn | $ZnSO_4 \cdot 7H_2O$ | 0.455 |
| Mo | $Na_2MoO_4 \cdot 2H_2O$ | 0 |
| Mn | $MnCl_2 \cdot 4H_2O$ | 0 |
| B | $H_3SO_3$ | 0 |
| Cu | $CuCl_2 \cdot 2H_2O$ | 0 |
| W | $Na_2WO_4 \cdot 2H_2O$ | 1.12 |
| K | KCl | 78.6 |
| Mg | $MgCl_2 \cdot 6H_2O$ | 29.9 |
| Na | NaCl | 78.7* |
| Ca | $CaCl_2 \cdot 2H_2O$ | 0** |
| Cysteine HCl | Cysteine HCl | 250 |
| P | $H_3PO_4/(NH_4)_2HPO_4$ | 279 |

*$Na^+$ concentration is from NaCl only. It does not include $Na^+$ from the other components such as $Na_2WO_4 \cdot 2H_2O$.
**$Ca^{+2}$ concentration does not include calcium from pantothenic acid, calcium salt.

The bioreactor was operated until the culture obtained a high productivity steady state. High productivity steady state was defined as ~3 g/L cell density, an ethanol concentration of >20 g/L, a CO uptake of >3.0 mmol/min, and a hydrogen uptake of >0.5 mmol/min.

The culture parameters of gas uptake, $H_2$ and CO, product concentrations and cell density were then monitored for any adverse affects. If the reduction in the component concentration did not affect those parameters after several (>3) cell retention times, the concentration would be reduced further. If after a reduction in a component's concentration a drop in the culture parameters was seen, the concentration would be increased back to a level that had previously shown to be adequate. If the culture recovered, the concentration would be lowered again, sometimes to the same level as before to repeat the effect, sometime to a level somewhere in between what worked and what caused problems.

Molybdenum requirement testing was started at t=0 hours by eliminating $Na_2MoO_4.2H_2O$ from the medium preparation. Just prior to removing those components, the culture conditions/parameters were as follows:

Cell density—3.2 g/L
CO Conversion—86%
$H_2$Conversion—36%
CO Uptake—3.0 mmol/min
$H_2$ Uptake—0.56 mmol/min
Ethanol—21.8 g/L
Total Acetyl—2.3 g/L
Butanol—0.32 g/L After ~9.7 cell retention times (292 hours) the molybdenum concentration in the culture broth had dropped to <0.0001% of the beginning concentration of 0.238 ppm Mo. The estimated remaining component concentrations in the broth were determined by washout calculations using a starting calcium concentration, MFR, LRT and any additions of Mo through either the medium or spikes into the bioreactor. There were no adverse affects on culture performance. After 292 hours with no molybdenum addition, the culture parameters/condition were as follows:

Cell density—2.9 g/L
CO Conversion—86%
$H_2$Conversion—36%
CO Uptake—3.0 mmol/min
$H_2$ Uptake—0.61 mmol/min
Ethanol—21.0 g/L
Total Acetyl—2.9 g/L
Butanol—0.32 g/L Example 7: Fermentation with Magnesium Limitations Experiments were conducted in a bioreactor (New Brunswick BioFlo I or IIc) operated as a straight through CSTR, with no cell recycle loop. Bioreactor operating conditions were as follows:

Culture type was *Clostridium ljungdahlii* C01.
Culture temperature was kept at 37-39° C.
Agitation was 880-890 rpm on an analog readout.
The unroused culture volume was 1275 ml.
Roused culture volume was ~1900 ml.
The culture pH set point was 4.2. A solution of 7.7% $NaHCO_3$ was used for pH control.
Feed gas was a synthetic blend of 15% $H_2$, 45% $N_2$, 30% CO and 10% $CO_2$ fed to the culture at a rate of 232 ml/min.
Medium was fed into the reactor at ~0.70 ml/min, or ~1008 ml/day.
Liquid and cell retention times were approximately 29-31 hours.
The medium used was as described below.

| Component/Ion | Added As | Conc in Med (ppm) |
|---|---|---|
| $NH_4^+$ | $NH_4Cl/(NH_4)_2HPO_4$ | 838 |
| Fe | $FeCl_2 \cdot 4H_2O$ | 16.8 |
| Ni | $NiCl_2 \cdot 6H_2O$ | 0.198 |
| Co | $CoCl_2 \cdot 6H_2O$ | 0.991 |
| Se | $Na_2SeO_3$ | 0.0913 |
| Zn | $ZnSO_4 \cdot 7H_2O$ | 0.455 |
| Mo | $Na_2MoO_4 \cdot 2H_2O$ | 0.238 |
| Mn | $MnCl_2 \cdot 4H_2O$ | 0.167 |
| B | $H_3BO_3$ | 1.05 |
| Cu | $CuCl_2 \cdot 2H_2O$ | 0.149 |
| W | $Na_2WO_4 \cdot 2H_2O$ | 1.12 |
| K | KCl | 78.6 |
| Mg | $MgCl_2 \cdot 6H_2O$ | 7.47-14.9 |
| Na | NaCl | 78.7* |
| Ca | $CaCl_2 \cdot 2H_2O$ | 0 |
| Cysteine HCl | Cysteine HCl | 250 |
| $PO_4^{-2}$ | $H_3PO_4/(NH_4)_2HPO_4$ | 816 |
| Pantothenic Acid | Pantothenic Acid | 0.0505 |
| Biotin | Biotin | 0.0400 |
| Thiamin | Thiamine | 0.1000 |

$Na^+$ concentration is from NaCl only. It does not include $Na^+$ from the other components such as $Na_2WO_4 \cdot 2H_2O$.

The bioreactor was operated until the culture obtained a high productivity steady state. High productivity steady state was defined as ~2.5-3 g/L cell density, an ethanol concentration of >20 g/L, a CO uptake of >3.0 mmol/min, and a hydrogen uptake of >0.5 mmol/min.

The culture parameters of gas uptake, $H_2$ and CO, product concentrations and cell density were then monitored for any adverse affects. If the reduction in the component concentration did not affect those parameters after several (>3) cell retention times, the concentration would be reduced further. If after a reduction in a component's concentration a drop in the culture parameters was seen, the concentration would be increased back to a level that had previously shown to be adequate. If the culture recovered, the concentration would be lowered again, sometimes to the same level as before to repeat the effect, sometime to a level somewhere in between what worked and what caused problems.

At the beginning of the experiment the magnesium concentration was at normal ethanol medium levels, or 59.77 ppm. Culture parameters were stable at ~3.1 g/L cell density; 20.5 g/L ethanol; 3.0 g/L acetyl; 2.4 mmol/min CO uptake; and 0.42 mmol/min $H_2$ uptake. The magnesium concentration was decreased to 14.97 ppm in the medium starting at t=0 hours. As the magnesium was washing out of the fermentor, all parameters were monitored for potential effects on culture performance. After ~300 hours or ~10 cell retention times, there was no observed detrimental effects on culture performance. There was an almost immediate drop in acetyl concentration after the decrease in magnesium, but this was due to a medium feed problem. Once the problem was corrected, the acetyl concentration increased back to levels similar to those seen when Mg concentration was at 59.77 ppm. It was concluded that a medium feed containing 14.97 ppm Mg was able to sustain a culture at ~3 g/L cell density at a ~30 hour cell retention time.

Mg at 59.77 ppm
Cell density—3.1 g/L
CO Conversion—84%
$H_2$Conversion—32%
CO Uptake—2.4 mmol/min
$H_2$ Uptake—0.42 mmol/min
Ethanol—20.5 g/L
Total Acetyl—2.4 g/L
Mg at 14.94 ppm
Cell density—3.0 g/L
CO Conversion—84%
$H_2$Conversion—34%

CO Uptake—2.4 mmol/min
H$_2$ Uptake—0.45 mmol/min
Ethanol—21.0 g/L
Total Acetyl—2.7 g/L The magnesium concentration was decreased further to 7.47 ppm in the medium starting at t=403 hours. As the magnesium was washing out of the fermentor, all parameters were monitored for potential effects on culture performance. After only 20 hours the hydrogen conversion and uptake began to decrease. The calculated Mg concentration in the culture was ~11 ppm. The culture performance continued to decline with dropping CO conversions/uptake, increasing acetyl concentration, decreasing ethanol concentration and a steady drop in cell density despite several additions of magnesium to both the culture and medium. The culture was eventually lost. It was concluded that a medium feed containing 7.47 ppm Mg was not sufficient to sustain a 3 g/l culture at a 30 hour cell retention time.

Example 8: Fermentation with Potassium Limitations

Experiments were conducted in a bioreactor (New Brunswick BioFlo I or IIc) operated as a straight through CSTR, with no cell recycle loop. Bioreactor operating conditions were as follows:

Culture type was *Clostridium ljungdahlii* C01.
Culture temperature was kept at 38-39° C.
Agitation was 950-1000 rpm on an analog readout.
Roused culture volume was ~1550 ml.
The culture pH set point was 4.2. A solution of 7.5% NaHCO$_3$ was used for pH control.
Feed gas was a synthetic blend of 15% H$_2$, 45% N$_2$, 30% CO and 10% CO$_2$ fed to the culture at a rate of 279 ml/min.
Medium was fed into the reactor at ~0.80-0.85 ml/min, or ~1220 ml/day.
Liquid and cell retention times were approximately 28-30 hours.
The medium used was as described below.

| Component/Ion | Added As | Conc in Med (ppm) |
|---|---|---|
| NH$_4^+$ | NH$_4$Cl/(NH$_4$)$_2$HPO$_4$ | 838 |
| Fe | FeCl$_2$•4H$_2$O | 16.8 |
| Ni | NiCl$_2$•6H$_2$O | 0.198 |
| Co | CoCl$_2$•6H$_2$O | 0.991 |
| Se | Na$_2$SeO$_3$ | 0.0456 |
| Zn | ZnSO$_4$•7H$_2$O | 0.455 |
| Mo | Na$_2$MoO$_4$•2H$_2$O | 0 |
| Mn | MnCl$_2$•4H$_2$O | 0 |
| B | H$_3$BO$_3$ | 0 |
| Cu | CuCl$_2$•2H$_2$O | 0 |
| W | Na$_2$WO$_4$•2H$_2$O | 1.12 |
| K | KCl | 39.3-118 |
| Mg | MgCl$_2$•6H$_2$O | 59.8 |
| Na | NaCl | 0* |
| Ca | CaCl$_2$•2H$_2$O | 0 |
| Cysteine HCl | Cysteine HCl | 250 |
| PO$_4^{-2}$ | H$_3$PO$_4$/(NH$_4$)$_2$HPO$_4$ | 816 |
| Pantothenic Acid | Pantothenic Acid | 0.0151 |
| Biotin | Biotin | 0.012 |
| Thiamin | Thiamine | 0.030 |

*Na$^+$ concentration is from NaCl only. It does not include Na$^+$ from the other components such as Na$_2$WO$_4$•2H$_2$O.

The bioreactor was operated until the culture obtained a high productivity steady state. High productivity steady state was defined as ~2.5-3 g/L cell density, an ethanol concentration of >20 g/L, a CO uptake of >3.0 mmol/min, and a hydrogen uptake of >0.5 mmol/min.

The culture parameters of gas uptake, H$_2$ and CO, product concentrations and cell density were then monitored for any adverse affects. If the reduction in the component concentration did not affect those parameters after several (>3) cell retention times, the concentration would be reduced further. If after a reduction in a component's concentration a drop in the culture parameters was seen, the concentration would be increased back to a level that had previously shown to be adequate. If the culture recovered, the concentration would be lowered again, sometimes to the same level as before to repeat the effect, sometime to a level somewhere in between what worked and what caused problems.

At the beginning of the experiment the potassium concentration was at normal ethanol medium levels, or 78.7 ppm. Culture parameters were stable at ~3 g/L cell density; ~22 g/L ethanol; ~2.6 g/L acetyl; 0.5 g/L butanol; 3.1 mmol/min CO uptake; and 0.5-0.6 mmol/min H$_2$ uptake. The potassium was reduced to 39.3 ppm in the medium starting at t=0 hours. As the potassium was washing out of the fermentor, the culture parameters were monitored for changes. After approximately 30 hours, the H$_2$ uptake began to drop followed by a drop in CO uptake. Hydrogen uptake dropped to 0.078 mmol/min and CO uptake dropped to a low of 2.8 mmol/min. The acetic acid concentration also decreased to a low of 0.78 g/L approximately 40 hours after the potassium reduction followed by a drop in ethanol concentration to 19.2 g/L. Butanol concentrations increased to 0.67 g/L. Cell density was also affected as seen by a decrease to 2.3 g/L, but that may have been the result of an unintentional cell retention time decrease to 27 hours immediately after the drop in potassium. Potassium was added into the reactor to raise the concentration to 78.7 ppm. The effect was immediately seen as an increase in CO uptake, H$_2$ uptake, ethanol and acid concentration. Butanol levels slowly decreased back down to ~0.53 g/L with the increase in potassium.

Once the culture had seemed to recover back to levels observed before potassium was limited, the potassium concentration in the medium was dropped to 59.0 ppm at t=139 hours. Again, culture parameters were monitored for any changes. As before the H$_2$ uptake began to decrease ~8 hours after the reduction of potassium. However, this time the CO uptake was not affected. There was a small increase in butanol to ~0.57 g/L. There was a drop in acetic acid concentration, but this was a continuation of a decreasing trend that was seen before the drop in potassium levels. Ethanol levels remained ~22 g/L. Cell density showed a small drop with the decrease in potassium levels from approximately 3.0 g/L to 2.8 g/L. The scatter in the data allowed for only approximate cell density concentrations to be reported. Potassium was added into the reactor to raise the concentration to 78.7 ppm. The effect was immediately seen as an increase in H$_2$ uptake, ethanol concentration, acid concentration and cell density confirming that the culture was potassium limited.

The overall effect of dropping potassium to 59.0 ppm was smaller than it was dropped to 39.3 ppm, but that level was still considered limiting. A potassium level of 78.7 ppm in the medium was therefore considered close to limiting. To determine if that level was indeed limiting, the potassium concentration in the medium was increased to 98.3 ppm at t=243 hours. With the increase in potassium, the H$_2$ uptake rose from ~0.61 mmol/min to ~0.71 mmol/min. There was also an increase in cell density from ~3.0 to ~3.3 g/l. Acetic acid was higher at ~3.3 g/L as compared to 2.6 when potassium was at 78.7 ppm. Butanol concentrations were more or less constant within the scatter of the data. Ethanol levels seemed to show a small increase to 24 g/l, but the scatter of the data made it difficult to determine. Since there was some positive effects from increasing the potassium to 98.3 ppm, the potassium concentration was increased further to 118 ppm at t=375 hours. The only definitive effect seen on culture parameters was a further cell density increase to ~3.9 g/L. All other parameters remained constant within the scatter of the data.

Example 9: Fermentation with Cysteine Limitations

Experiments were conducted in a bioreactor (New Brunswick BioFlo I or IIc) operated as a straight through CSTR, with no cell recycle loop. Bioreactor operating conditions were as follows:
Culture type was *Clostridium ljungdahlii* C01.
Culture temperature was kept 38-39° C.
Agitation was 900 rpm on an analog readout.
Roused culture volume was ~1650 ml.
The culture pH set point was 4.5. A solution of 7.5% $NaHCO_3$ was used for pH control.
Feed gas was a synthetic blend of 15% $H_2$, 45% $N_2$, 30% CO and 10% $CO_2$ fed to the culture at a rate of 279 ml/min.
Medium was fed into the reactor at ~0.83-0.86 ml/min, or ~1220 ml/day.
Liquid and cell retention times were approximately 28-30 hours.
The medium used was as described below.

| Component/ Ion | Added As | Conc in Med (ppm) |
|---|---|---|
| $NH_4^+$ | $NH_4Cl/(NH_4)_2HPO_4$ | 838 |
| Fe | $FeCl_2 \cdot 4H_2O$ | 16.8 |
| Ni | $NiCl_2 \cdot 6H_2O$ | 0.198 |
| Co | $CoCl_2 \cdot 6H_2O$ | 0.991 |
| Se | $Na_2SeO_3$ | 0.0456 |
| Zn | $ZnSO_4 \cdot 7H_2O$ | 0.455 |
| Mo | $Na_2MoO_4 \cdot 2H_2O$ | 0 |
| Mn | $MnCl_2 \cdot 4H_2O$ | 0 |
| B | $H_3BO_3$ | 0 |
| Cu | $CuCl_2 \cdot 2H_2O$ | 0 |
| W | $Na_2WO_4 \cdot 2H_2O$ | 1.12 |
| K | KCl | 78.7 |
| Mg | $MgCl_2 \cdot 6H_2O$ | 59.8 |
| Na | NaCl | 0* |
| Ca | $CaCl_2 \cdot 2H_2O$ | 0 |
| Cysteine HCl | Cysteine HCl | 125-250 |
| $PO_4^{-2}$ | $H_3PO_4/(NH_4)_2HPO_4$ | 816 |
| Pantothenic Acid | Pantothenic Acid | 0.0353 |
| Biotin | Biotin | 0.028 |
| Thiamin | Thiamine | 0.070 |

*$Na^+$ concentration is from NaCl only. It does not include $Na^+$ from the other components such as $Na_2WO_4 \cdot 2H_2O$.

At the beginning of the experiment, the cysteine concentration was at normal ethanol medium levels, or 250 ppm. Culture parameters were stable at ~3 g/L cell density; 23 g/L ethanol; 2.4 g/L acetyl; 3.1 mmol/min CO uptake; and 0.56 mmol/min $H_2$ uptake. The cysteine was decreased to 187.5 ppm in the medium starting at t=0 hours. As the cysteine was washing out of the fermentor, all parameter was monitored for signs of limitation. The cysteine concentration was held at that level for 167 hours or 5 XRTs. All parameters remained constant. A 187.5 ppm concentration of cysteine was enough to sustain a 3 g/L culture with a 33 hours cell retention time.

The cysteine concentration was decreased further in the medium from 187.5 ppm to 125 ppm at t=167 hours. Almost immediately, the $H_2$ uptake and conversions began to drop along with a decreasing acetic acid concentration. CO uptake and conversions and cell density were constant. The $H_2$ uptake dropped to 0.36 mmol/min, $H_2$ conversion dropped to 21% and acetic acid decreased to 1.7 g/L. Cysteine concentration in both the medium and bioreactor were increased to 187.5 ppm then 250 ppm. The culture quickly recovered. A concentration of 125 ppm of cysteine was not sufficient to sustain a 3 g/L culture at a 33 hour cell retention time.

After the culture had fully recovered, the cysteine limitation was tested again. At t=407 hrs, the cysteine in the medium was dropped to 162.5 ppm. As seen before, the $H_2$ conversions and uptake began dropping almost immediately. The acetic acid concentration again dropped but not as quickly or as far as when the cysteine concentration was 125 ppm. The $H_2$ uptake dropped to 0.49 mmol/min, $H_2$ conversion dropped to 29% and acetic acid decreased from 3.0 to 2.7 g/L. A concentration of 162.5 ppm of cysteine was not sufficient to sustain a 3 g/L culture at a 33 hour cell retention time.

Example 10: Fermentation with Thiamine Limitations

Experiments were conducted in a bioreactor (New Brunswick BioFlo I or IIc) operated as a straight through CSTR. Bioreactor operating conditions were as follows:
Culture type was *Clostridium ljungdahlii* C01.
Culture temperature was kept at 38-39° C.
Agitation was 950 rpm on an analog readout.
Roused culture volume was ~1950 ml.
The culture pH set point was 4.5. A solution of 7.5% $NaHCO_3$ was used for pH control.
Feed gas was a synthetic blend of 15% $H_2$, 45% $N_2$, 30% CO and 10% $CO_2$ fed to the culture at a rate of 279 ml/min.
Medium was fed into the reactor at ~0.84-0.86 ml/min, or ~1220 ml/day.
Liquid and cell retention times were approximately 30-32 hours.
The medium used was as described below

| Component/ Ion | Added As | Conc in Med (ppm) |
|---|---|---|
| $NH_4^+$ | $NH_4Cl/(NH_4)_2HPO_4$ | 654 |
| Fe | $FeCl_2 \cdot 4H_2O$ | 8.4 |
| Ni | $NiCl_2 \cdot 6H_2O$ | 0.198 |
| Co | $CoCl_2 \cdot 6H_2O$ | 0.991 |
| Se | $Na_2SeO_3$ | 0.012 |
| Zn | $ZnSO_4 \cdot 7H_2O$ | 0.455 |
| Mo | $Na_2MoO_4 \cdot 2H_2O$ | 0 |
| Mn | $MnCl_2 \cdot 4H_2O$ | 0 |
| B | $H_3BO_3$ | 0 |
| Cu | $CuCl_2 \cdot 2H_2O$ | 0 |
| W | $Na_2WO_4 \cdot 2H_2O$ | 1.12 |
| K | KCl | 78.7 |
| Mg | $MgCl_2 \cdot 6H_2O$ | 14.8 |
| Na | NaCl | 0* |
| Ca | $CaCl_2 \cdot 2H_2O$ | 0 |
| Cysteine HCl | Cysteine HCl | 250 |
| $PO_4^{-2}$ | $H_3PO_4/(NH_4)_2HPO_4$ | 384 |
| Pantothenic Acid | Pantothenic Acid | 0.283 |
| Biotin | Biotin | 0.0070 |
| Thiamin | Thiamine | 0.0105 |

*$Na^+$ concentration is from NaCl only. It does not include $Na^+$ from the other components such as $Na_2WO_4 \cdot 2H_2O$.

The vitamin solution normally added to the medium was a solution of 0.0505 g/L pantothenate, 0.040 g/L biotin and 0.10 g/L thiamine. For this study, the vitamin solution was separated into three solutions, one for each component. The concentrations of those solutions were kept the same as in the original vitamin mix. This way the concentration of each component could be adjusted as needed without changing the other vitamin concentrations.

At the beginning of this experiment, the pantothenic acid concentration in the medium was 0.03535 ppm or 0.7 ml of a 0.0505 g/L pantothenic acid solution per liter of medium. The biotin concentration in the medium was 25% of the normal vitamin concentration or 0.0070 ppm in the medium. This was the equivalent of 0.175 ml of the 0.04 g/L biotin solution added per liter of medium. The thiamine level in the medium was 25% of the normal vitamin concentration, or 0.0175 ppm. This was the equivalent of 0.175 ml of a 0.10 g/L thiamine solution added per liter of medium. At t=0 hrs, the thiamine concentration in the medium was dropped to 15% of normal, or 0.0105 ppm. There was no immediate effect seen on the cell density. However, the $H_2$ uptake, total acetyl concentration, and ethanol concentration all started to drop almost immediately indicating that the previous thiamine concentration of 0.0175 ppm was already close to limiting. At the same time the CO uptake increased slightly from 3.1 to 3.2 mmol/min. This may be an indication of an increase in mass transfer during that time even though the agitation rate remained constant. To verify the cause of the drop in culture productivity, 0.5 ml of the pantothenic acid solution was first added to the reactor at t=43 hrs. When this had no affect on the culture, 0.115 ml of the thiamine solution was added back to the reactor at t=84 his to raise the thiamine level in the reactor to ~0.0175 ppm. This had an immediate affect on the culture. Hydrogen uptake, acid levels, and ethanol concentration all started to increase. The culture needed the additional thiamine. No further changes to the reactor were made in order to wash the added pantothenic acid and thiamine out of the reactor back down to the 0.0354 ppm pantothenic acid and 0.0105 ppm thiamine coming in from medium addition. Over the following 228 hrs as the vitamins washed out, the $H_2$ uptake first increased to ~0.53 mmol/min then dropped to a low of ~0.31 mmol/min supposedly as the extra pantothenate and thiamine washed back out of the reactor. However, with no changes to the vitamin levels or any other culture changes, the $H_2$ uptake started to steadily increase reaching ~0.5 mmol/min around t=273 hrs. The acid and ethanol concentrations did not follow a set pattern but varied around 25 g/L ethanol and 1.1-2.4 g/L acid. The CO uptake remained constant at 3.2 mmol/min, and the cell density held fairly constant at 2.8-3.0 g/L.

At the beginning of the experiment when the thiamine level in the medium was dropped from 0.0175 ppm to 0.0105 ppm, the effect on the culture's parameters was almost immediate indicating that the 0.0175 ppm thiamine level was close to limiting already. The calculated parameters used to better correlate nutrient addition verses culture performance before the drop to 0.0105 ppm thiamine were as follows: The µg thiamine added per mmol of gas uptake was ~0.0041 µg/mmol. The µg of thiamine added per gram of cells produced was ~6.5 µg/g. Further confirmation that the thiamine was indeed limiting at 0.0105 ppm was the immediate improvement in culture parameters when the thiamine level in the reactor was temporarily increased to 0.0175 ppm in the reactor.

While the invention herein disclosed has been described by means of specific aspects, examples and applications thereof, numerous modifications and variations could be made thereto by those skilled in the art without departing from the scope of the invention set forth in the claims.

What is claimed is:

1. A fermentation process comprising fermenting syngas in a fermentation medium with acetogenic bacteria, the process effective for providing a specific STY of at least about 1 gram of ethanol/(L·day·gram cells),
   wherein the fermentation medium includes
      at least 112 to 125 mg of nitrogen per gram of cells,
      at least 10.5 to 15 mg of phosphorous per gram of cells, and
      at least 26 to 36 mg of potassium per gram of cells,
   wherein the fermentation medium has less than 0.025 ppm boron, less than 0.0025 ppm manganese, less than 0.001 ppm molybdenum, and less than 0.01 ppm copper and wherein the fermentation medium has less than 0.01 g/L carbohydrates and less than 0.01 g/L yeast extract.

2. The fermentation process of claim 1 wherein the nitrogen is provided from a nitrogen source selected from the group consisting of ammonium chloride, ammonium phosphate, ammonium sulfate, ammonium nitrate, and mixtures thereof, the phosphorous is provided from a phosphorous source selected from the group consisting of phosphoric acid, ammonium phosphate, potassium phosphate, and mixtures thereof, and the potassium is provided from a potassium source selected from the group consisting of potassium chloride, potassium phosphate, potassium nitrate, potassium sulfate, and mixtures thereof.

3. The fermentation process of claim 1 wherein the fermentation medium includes one or more of
   at least about 2.7 mg of iron per gram of cells,
   at least about 10 µg of tungsten per gram of cells,
   at least about 34 µg of nickel per gram of cells,
   at least about 9 µg of cobalt per gram of cells,
   at least about 4.5 mg of magnesium per gram of cells,
   at least about 11 mg of sulfur per gram of cells, and
   at least about 6.5 µg of thiamine per gram of cells.

4. The fermentation process of claim 3 wherein the fermentation medium includes one or more of
   about 2.7 to about 5 mg of iron per gram of cells,
   about 10 to about 30 µg of tungsten per gram of cells,
   about 34 to about 40 µg of nickel per gram of cells,
   about 9 to about 30 µg of cobalt per gram of cells,
   about 4.5 to about 10 mg of magnesium per gram of cells,
   about 11 to about 20 mg of sulfur per gram of cells, and
   about 6.5 to about 20 µg of thiamine per gram of cells.

5. The fermentation process of claim 4 wherein the iron is provided from an iron source selected from the group consisting of ferrous chloride, ferrous sulfate, and mixtures thereof, the tungsten is provided from a tungsten source selected from the group consisting of sodium tungstate, calcium tungstate, potassium tungstate, and mixtures thereof, the nickel is provided from a nickel source selected from the group consisting of nickel chloride, nickel sulfate, nickel nitrate, and mixtures thereof, the cobalt is provided from a cobalt source selected from the group consisting of cobalt chloride, cobalt fluoride, cobalt bromide, cobalt iodide, and mixtures thereof, the magnesium is provided from a magnesium source selected from the group consisting of magnesium chloride, magnesium sulfate, magnesium phosphate, and the sulfur is provided from a sulfur source selected from the group consisting of cysteine, sodium sulfide, and mixtures thereof.

6. The fermentation process of claim 1 wherein a pH of the fermentation medium is maintained in a range of about 4.2 to about 4.8.

7. The fermentation process of claim 1 wherein the syngas has a $CO/CO_2$ ratio of at least about 0.75.

8. The fermentation process of claim 1 wherein the acetogenic bacteria is selected from the group consisting of *Acetogenium kivui, Acetoanaerobiun noterae, Acetobacterium woodii, Alkalibaculum bacchi* CP11 ATCC BAA-1772, *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium autoethanogenum* DSM 19630 of DSMZ Germany, *Clostridium autoethanogenum* DSM 10061 of DSMZ Germany, *Clostridium autoethanogenum* DSM 23693 of DSMZ Germany, *Clostridium autoethanogenum* DSM 24138 of DSMZ Germany, *Clostridium carboxidivorans* P7 ATCC PTA-7827, *Clostridium coskatii* ATCC PTA-10522, *Clostridium drakei, Clostridium ljungdahlii* PETC ATCC 49587, *Clostridium ljungdahlii* ERI2 ATCC 55380, *Clostridium ljungdahlii* C-01 ATCC 55988, *Clostridium ljungdahlii* O-52 ATCC 55889, *Clostridium magnum, Clostridium pasteurianum* DSM 525 of DSMZ Germany, *Clostridium ragsdali* P11 ATCC BAA-622, *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and mixtures thereof.

9. The fermentation process of claim 1 wherein the process is effective for providing a cell density of at least about 1.0 g/L.

10. The fermentation process of claim 1 wherein the process is effective for providing a CO conversion of at least about 5 to about 99%.

11. The fermentation process of claim 1 wherein B, Mn, Mo or Cu sources are eliminated from medium preparations.

* * * * *